US012758423B2

(12) United States Patent
Kim

(10) Patent No.: US 12,758,423 B2
(45) Date of Patent: Oct. 13, 2026

(54) OPHTHALMIC TREATMENT APPARATUS AND CONTROL METHOD THEREFOR

(71) Applicant: LUTRONIC CORPORATION, Goyang (KR)

(72) Inventor: Jong Min Kim, Seoul (KR)

(73) Assignee: R:GEN VISION, INC., Boston, MA (US)

( * ) Notice: Subject to any disclaimer, the term of this patent is extended or adjusted under 35 U.S.C. 154(b) by 1220 days.

(21) Appl. No.: 17/043,986

(22) PCT Filed: Apr. 2, 2019

(86) PCT No.: PCT/KR2019/003837
§ 371 (c)(1),
(2) Date: Sep. 30, 2020

(87) PCT Pub. No.: WO2019/194519
PCT Pub. Date: Oct. 10, 2019

(65) Prior Publication Data

US 2021/0030588 A1 Feb. 4, 2021

(30) Foreign Application Priority Data

Apr. 3, 2018 (KR) ........................ 10-2018-0038748

(51) Int. Cl.
*A61F 9/008* (2006.01)
*A61B 17/00* (2006.01)

(52) U.S. Cl.
CPC .... *A61F 9/008* (2013.01); *A61B 2017/00057* (2013.01); *A61B 2017/00115* (2013.01); *A61B 2017/00154* (2013.01); *A61F 2009/00844* (2013.01); *A61F 2009/00872* (2013.01);
(Continued)

(58) Field of Classification Search
CPC .......... A61B 18/22; A61B 2017/00057; A61B 2017/00115; A61B 2017/00154; A61B 2018/2253; A61F 9/008; A61F 9/00821; A61F 2009/00844; A61F 2009/00863;
(Continued)

(56) References Cited

U.S. PATENT DOCUMENTS 7,836,894 B2 11/2010 Brinkmann et al.
2006/0111697 A1 5/2006 Brinkmann et al.
(Continued)

FOREIGN PATENT DOCUMENTS

JP 2000350742 A 12/2000
JP 2007506472 A 3/2007
(Continued)

*Primary Examiner* — Niketa Patel
*Assistant Examiner* — Shreya Anjaria

(57) ABSTRACT

The present invention relates to an ophthalmic treatment apparatus and a control method therefor, and the present invention provides an ophthalmic treatment apparatus comprising: a treatment light generation unit for generating a treatment light which is radiated to a treatment area of an eye tissue; a sensing unit for sensing a signal generated as the state of the tissue changes due to each treatment light radiated to the tissue of the treatment area; and a guide unit for displaying, to a user, information about damage to the tissue caused by each treatment light radiated on the basis of the signal sensed by the sensing unit.

11 Claims, 11 Drawing Sheets

(52) U.S. Cl.
CPC ............... *A61F 2009/00887* (2013.01); *A61F 2009/00891* (2013.01)

(58) Field of Classification Search
CPC .. A61F 2009/00872; A61F 2009/00887; A61F 2009/00891; A61F 2009/00897
See application file for complete search history.

(56) References Cited

U.S. PATENT DOCUMENTS

| | | | | |
|---|---|---|---|---|
| 2007/0213693 | A1* | 9/2007 | Plunkett | A61F 9/008 606/4 |
| 2013/0110093 | A1* | 5/2013 | Yee | A61F 9/00821 606/4 |
| 2013/0261612 | A1 | 10/2013 | Yokosuka et al. | |
| 2015/0297675 | A1* | 10/2015 | Osborne | A61K 38/17 604/20 |
| 2015/0366705 | A1* | 12/2015 | Ha | A61F 9/008 606/6 |
| 2016/0331585 | A1* | 11/2016 | Kim | A61F 9/008 |
| 2017/0202619 | A1* | 7/2017 | Lim | A61B 5/6858 |
| 2017/0266041 | A1 | 9/2017 | Kim et al. | |

FOREIGN PATENT DOCUMENTS

| | | | | |
|---|---|---|---|---|
| JP | 2012213634 | A | 11/2012 | |
| KR | 101417843 | B1 | 7/2014 | |
| KR | 101814444 | B1 | 1/2018 | |
| KR | 20180012524 | A | 2/2018 | |
| WO | WO-2016018099 | A1 * | 2/2016 | A61F 9/00 |
| WO | WO2018021780 | A1 | 2/2018 | |

* cited by examiner

OPHTHALMIC TREATMENT APPARATUS AND CONTROL METHOD THEREFOR

TECHNICAL FIELD

The present disclosure relates to an ophthalmic treatment apparatus and a control method therefor and, more particularly, to an ophthalmic treatment apparatus and a control method therefor, that can guide treatment contents to a user.

BACKGROUND ART

Recently, the technology of treating a lesion by radiating beams to a body tissue and thereby changing the state of a tissue is widely applied. In particular, a laser treatment technology is widely used for various lesions related to the eyes. For example, an apparatus for treating the lesion of an anterior eye segment, such as keratoplasty, glaucoma treatment, or cataract surgery, is widely commercialized. Recently, an apparatus for treating a lesion occurring in an eyeground area, such as macular degeneration, is being developed.

Such a treatment apparatus radiates a laser to a target tissue to transmit energy thereto, thus leading to a chance in a state of the tissue. However, if the energy is excessively transmitted to the target tissue, even an adjacent tissue may be damaged. Especially when the lesion of the eye is treated, the excessive energy may cause impaired vision, so that it may be fatal. In contrast, there is a problem that treatment is not performed properly, when sufficient energy is not transmitted to the target tissue. Particularly, the amount of energy required for treatment may vary depending on a patient or a location of the target tissue in the case of the same patient. Therefore, an operator should adjust an energy level depending on a patient and a location of a lesion to perform treatment, but there is a limitation in performing optimized treatment by the operator's experience and intuition.

DISCLOSURE

Technical Problem

The present disclosure is to provide an ophthalmic treatment apparatus and a control method therefor, in which information about treatment by a treatment beam during treatment is provided to a user in real time, so that the user may perform the treatment on the basis of the treatment information.

Technical Solution

In order to solve the aforementioned object, the present disclosure proposes an ophthalmic treatment apparatus including a treatment beam generation unit for generating a treatment beam which is radiated to a treatment area of an eye tissue; a sensing unit for sensing a signal generated as a state of the tissue changes due to each treatment beam radiated to the tissue of the treatment area; and a guide unit for displaying, to a user, information about damage to the tissue caused by each treatment beam radiated on the basis of the signal sensed by the sensing unit.

The ophthalmic treatment apparatus may further include a setting unit for setting at least one reference value used to display the information about damage to the tissue in the guide unit, and the guide unit may display the information about damage to the tissue by comparing it with the at least one reference value which is set through the setting unit.

The at least one reference value may be set using the signal sensed in the sensing unit, when a targeted state change occurs in the tissue of a test area due to the treatment beam while the treatment beam is radiated to the test area.

For instance, at least one reference value may be a signal value generated from the tissue when the tissue undergoes over treatment, and the guide unit may compare a signal sensed by the sensing unit during treatment with the reference value to display information about damage to the tissue to the user.

Moreover, the guide unit may suggest that the user lowers the intensity of the treatment beam, when it is determined that the tissue undergoes the over treatment on the basis of the signal sensed by the sensing unit.

Meanwhile, at least one reference value may include a first reference value corresponding to a signal value generated in the tissue when the tissue undergoes the over treatment, and a second reference value corresponding to a signal value generated in the tissue when energy is efficiently to the tissue. Furthermore, the guide unit may compare the signal sensed by the sensing unit during treatment with each of the first reference value and the second reference value to display the information about damage to the tissue to the user.

To be more specific, the guide unit may determine a grade section indicating a degree of damage to the tissue using the first reference value and the second reference value, and the degree of damage to the tissue caused by an associated treatment beam on the basis of the signal sensed by the sensing unit during the treatment may be indicated by the grade section.

In this regard, it may be set that a highest damage grade in the grade section includes the first reference value, and a lowest damage grade does not include the second reference value.

Meanwhile, the present disclosure provides a control method of an ophthalmic treatment apparatus, including operating a treatment beam generation unit to radiate a treatment beam to a treatment area of an eye tissue; Sensing, through a sensing unit, a signal which is generated when a state of the tissue in the treatment area is changed by the treatment beam; and displaying, through a guide unit, information about damage to the tissue caused by the treatment beam using the signal sensed through the sensing unit, to a user.

The control method may further include setting at least one reference value used to display the information about damage to the tissue, and the displaying of the damage information to the user may compare the at least one reference value with a signal value sensed through the sensing unit at the sensing to display the damage information to the user.

The setting of the at least one reference value may include radiating a treatment beam to a test area; sensing a signal generated from the test area by the treatment beam; and setting the reference value using a signal value sensed when a state of the test area is changed, if a targeted state change occurs in the tissue of the test area.

Alternatively, the setting of the at least one reference value may include setting a first reference value corresponding to a signal value generated when the tissue undergoes over treatment; and setting a second reference value corresponding to a signal value generated when energy is efficiently transmitted to the tissue.

In this regard, the setting of the first reference value may set the first reference value using a signal value sensed from the test area when a treatment beam is radiated to the test area and thereby white burn is observed in the eyeground.

The setting of the second reference value may set the second reference value using a signal value sensed from the test area when a treatment beam is radiated to the test area and thereby a change in state of the test area is observed by angiography.

Meanwhile, the present disclosure provides a treatment method using an ophthalmic treatment apparatus, including radiating a treatment beam to a test area of an eye tissue to measure a signal value as a state of the tissue is changed; setting a grade standard of the signal value generated depending on a degree of damage to the tissue on the basis of the measured signal value; radiating the treatment beam to a treatment area of the eye tissue; sensing a signal generated while the state of the tissue in the treatment area is changed by the treatment beam; and displaying information about damage to the tissue in the treatment area caused by the treatment beam, on the basis of the set grade standard.

Advantageous Effects

In accordance with the present disclosure, a user can perform treatment while monitoring a tissue damage degree in a location where treatment is performed, so that the treatment can be performed using a treatment beam of a proper output in each location.

Furthermore, when over treatment is performed or treatment is not sufficiently performed, this can be guided to a user, thus minimizing damage to a tissue, and preventing treatment from being omitted.

MODE FOR DISCLOSURE

Hereinafter, an ophthalmic treatment apparatus and a control method therefor in accordance with an embodiment of the present disclosure will be described in detail with reference to the accompanying drawings. In the following description, the positional relationship between respective components will be described with reference to the drawings in principle. The drawings may be shown by simplifying the structure of the disclosure for the convenience of description or exaggerating if necessary. However, the present disclosure is not limited thereto. In addition, various devices may be added, changed or omitted.

As the ophthalmic treatment apparatus that will be described below, an apparatus for treating an eyeground lesion will be mainly described. However, the present disclosure may also be applied to a treatment apparatus for treating the eyeground lesion as well as other ophthalmic lesions. For example, the present disclosure may be applied to an apparatus for treating the lesion of the anterior eye segment, such as glaucoma, and be applied to an apparatus for treating the lesion occurring in a crystalline lens, such as cataract. Moreover, it should be noted that the present disclosure may be widely used in a treatment apparatus for treating lesions of other medical branches, such as a skin lesion, as well as the ophthalmic lesion.

Hereinafter, the term 'treatment area' is an area in which treatment is required, and may refer to an area as a section, having a predetermined area or a predetermined length. Furthermore, the term 'treatment location' is a location where treatment is located in the treatment area, and may refer to a location as a spot located at a specific coordinate. Moreover, the term 'target tissue' may refer to a tissue that is to be treated. When a plurality of tissues forms, a layered structure depending on the depth of a specific treatment location, the target tissue may be a tissue located in all or some of a depth section.

In other words, if a beam is radiated to the specific 'treatment location' in the shape of a spot, most of energy may be transmitted to the 'target tissue' located in the specific depth section of the corresponding treatment location. Furthermore, in order to treat the 'treatment area' of the predetermined area, treatment may be performed by sequentially radiating a beam to a plurality of 'treatment locations' located in the treatment area.

Figure 1:
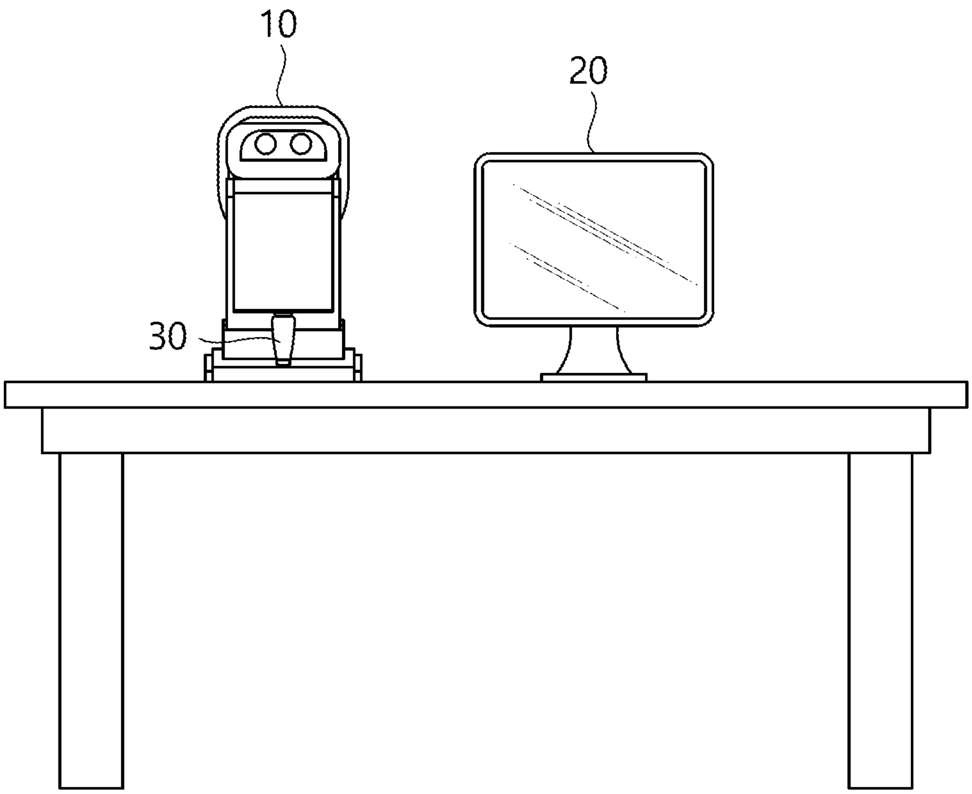
FIG. 1 is a perspective view schematically illustrating an ophthalmic treatment apparatus in accordance with an embodiment of the present disclosure.

FIG. 1 is a perspective view schematically illustrating an ophthalmic treatment apparatus in accordance with an embodiment of the present disclosure. The ophthalmic treatment apparatus in accordance with this embodiment is an apparatus for performing treatment by radiating a treatment beans to the eyeground, and includes a slit lamp 10 and an interface unit 20 as illustrated in FIG. 1.

The slit lamp 10 is a device configured such that a user performs treatment while observing a patient's eye. An object part 180 is provided on a first side of a body of the slit lamp 10 to fix the location of the patient's eye. Furthermore an eyepiece part 170 at which a user's eye is located is provided on a second side to observe the patient's eye. Various components are provided in the slit lamp 10 to perform a treating operation, and will be described below in detail. An operation unit 30 may be provided outside the slit lamp to control the operation of the treatment apparatus. The operation unit 30 may be configured using a structure such as a keyboard, a joystick, or a pedal. The user may manipulate the operation unit 30 to manipulate a viewing direction of the slit lamp or the treatment operation of the treatment apparatus.

The interface unit 20 is provided adjacent to the slit lamp 10, displays various pieces of information required for the user during treatment, and is configured such that the user inputs/sets commands and information. As illustrated in FIG. 1, the interface unit 20 includes a display device such as a monitor. Furthermore, the interface unit may be configured to input information through a touch-screen function of a display device, or be provided with a separate input device such as a keyboard or a mouse.

Figure 2:
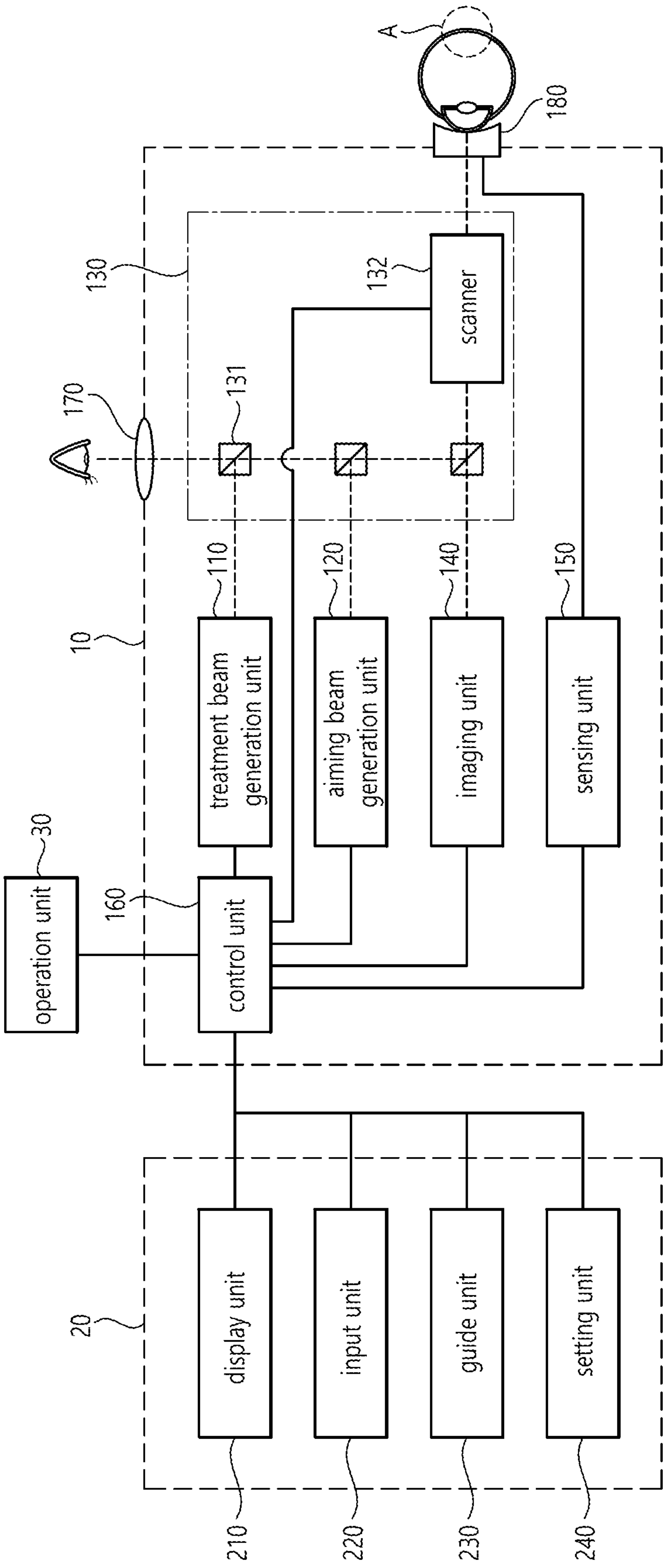
FIG. 2 is a block diagram schematically illustrating an internal component of the ophthalmic treatment apparatus of FIG. 1.

FIG. 2 is a block diagram schematically illustrating an internal component of the ophthalmic treatment apparatus of FIG. 1. The slit lamp 10 includes a treatment beam radiation unit that generates a treatment beam to radiate the treatment beam to the eyeground. The treatment beam radiation unit includes a treatment beam generation unit 110 that generates the treatment beam, and a beam delivery unit 130 that delivers a treatment beam generated from the treatment beam generation unit to the eyeground. Furthermore, the slit lamp may further include an aiming beam generation unit 120 to display a location where the treatment beam is radiated. Moreover, the slit lamp may further include an imaging unit 140 for photographing an image of a patient's eyeground, a sensing unit 150 for sensing information about a change in the state of the tissue by the treatment beam, and a control unit 160 for controlling various components.

The treatment beam generation unit 110 includes a treatment beam source (not illustrated) and various optical elements (not illustrated) that modulate the properties of a beam generated from the treatment beam source. The treatment beam source of this embodiment includes a laser medium such as Nd:YAG or Ho:YAG or a laser diode, thus generating the laser as the treatment beam. The parameter of the treatment beam, such as a wavelength, a pulse width, or an output, may be determined or adjusted in consideration of the contents of the lesion and the properties of the target tissue.

The beam delivery unit 130 is composed of a plurality of optical elements to form an optical path along which the treatment beam travels. Therefore, the treatment beam generated by the treatment beam generation unit 110 travels along the beam delivery unit 130 to be radiated to the eyeground.

Such a beam delivery unit 130 may form the optical path along which the treatment beam, an aiming beam and/or a photographing beam that will be described below travels. As illustrated in FIG. 2, the beam delivery unit 130 may be provided with at least one beam combiner 131, so that the aiming beam and/or the photographing beam may be joined on the optical path, and may be radiated to the eyeground. Furthermore, the aiming beam and/or the photographing beam reflected from the eyeground may travel through the beam delivery unit 130 in a reverse direction, so that the beam may travel to the eyepiece part 170 or be received by the imaging unit 140. However, the present disclosure is not limited thereto, and the aiming beam and/or the photographing beam may form a separate optical path distinguished from the radiation path of the treatment beam or may omit the optical path.

The beam delivery unit 130 includes a scanner 132 that changes a location where the beam is radiated. The scanner 132 includes at least one reflection member and a drive unit that rotates the reflection member. The scanner 132 may change the radiating location of the beam reflected by the reflection member, while rotating the reflection member. Furthermore, although not illustrated in FIG. 2, the beam delivery unit 130 may further include optical elements such as a plurality of optical lenses for focusing or dispersing the beam or an optical filter. The beam delivery unit 130 may adjust various parameters including the size of a spot where the treatment beam is radiated onto the treatment area using the optical elements.

An object part 180 is provided on an end of the beam delivery unit 130. The object part 180 is configured such that a patient's eye to be treated is located, and includes an object lens or a contact lens coming into contact with the patient's eye. Moreover, the object part may further include a suction device that fixedly sucks the anterior eye segment of the patient to fix the patient's eye.

Meanwhile, the aiming beam generation unit 120 generates the aiming beam. The aiming beam is radiated to the treatment location where the treatment beam is radiated, so that the operator can confirm the location where the treatment beam is radiated before the treatment beam is radiated or while the treatment beam is radiated, thus displaying the associated location. The aiming beam generated by the aiming beam generation unit 120 is radiated to the treatment area of the eyeground through the beam delivery unit 130. Here, the aiming beam has a wavelength in a visible-light band, and the user may check the wavelength through the eyepiece part and thereby confirm the location of the aiming beam.

However, when it is possible to confirm the location where the treatment beam is radiated on an eyeground image displayed on the interface unit, the aiming beam generation unit may be omitted.

Meanwhile, the imaging unit 140 is configured to acquire the image of the patient's treatment area. The imaging unit 140 includes an imaging element, and receives the photographing beam that is radiated by a photographing beam source (not illustrated) and is reflected from the eyeground, thus acquiring the eyeground image. The imaging unit 140 according to this embodiment is configured to acquire the eyeground image including the entire treatment area. In addition, the radiating location of the photographing beam may be changed through the scanner like the treatment beam, so that it is possible to acquire the image of an area adjacent to the radiating location of the treatment beam. Furthermore, although the ophthalmic treatment apparatus including the imaging unit has been described in this embodiment, the present disclosure is not limited thereto and the configuration corresponding to the imaging unit may be omitted.

Furthermore, the sensing unit 150 is configured to sense information about a change in the state of the tissue by the treatment beam when the treatment beam is radiated. The configuration and operation of the sensing unit will be described below in detail.

The control unit 160 is configured to control various components including the treatment beam generation unit 110, the aiming beam generation unit 120, the beam delivery unit 130, and the imaging unit 140, and controls various components on the basis of contents manipulated by the user through the operation unit 30 or contents inputted or set through the interface unit 20. Furthermore, the control unit 160 performs the function of receiving information about an image captured by the imaging unit 140 and information sensed by the sensing unit 150, modulating and calculating these pieces of information, and then transmitting the calculated result to another component.

Meanwhile, the interface unit 20 includes a display unit 210 and an input unit 220. Here, the display unit 210 is configured to display and transmit various pieces of information to the user, and the input unit 220 is configured such that the user transmits information and a command.

Here, the display unit 210 is composed of a display device capable of displaying various pieces of information including the image. The eyeground image that is photographed by the above-described imaging unit 140 or the eyeground image that is previously photographed by a separate eyeground camera or the like may be transmitted through the control unit 160 to be displayed on the display unit 210, and the user may see the image of the patient's eyeground through the display unit 210. Such an eyeground image may be variously utilized to confirm the position of the lesion before the treatment, set the radiating location of the treatment beam, or confirm the treatment result. Furthermore, various pieces of information as well as the eyeground image may be displayed to the user through the display unit.

The input unit 220 is configured such that die user transmits various pieces of information or the command to the treatment apparatus. Therefore, the user may input information about the patient, and information about the treatment through the input unit 220, may command the treatment operation, and may select a desired one from various options provided by the treatment apparatus. For example, the user may set the treatment area on the eyeground image displayed on the display unit 210 using the input unit 220, may select any one of treatment modes suggested by the treatment apparatus, or may select any one of treatment beam radiating patterns stored in the treatment apparatus. The input unit 220 may be configured to input various pieces of information using the separate input apparatus such as the keyboard or the mouse, or using the touch screen function of the display forming the display unit 210.

In such an ophthalmic treatment apparatus, the user determines the treatment location and the parameter of the treatment beam through the input unit 220 or the operation unit 30, and the control unit 160 controls the treatment operation of the treatment apparatus on the basis of the treatment location and the parameter of the treatment beam.

Figure 3:
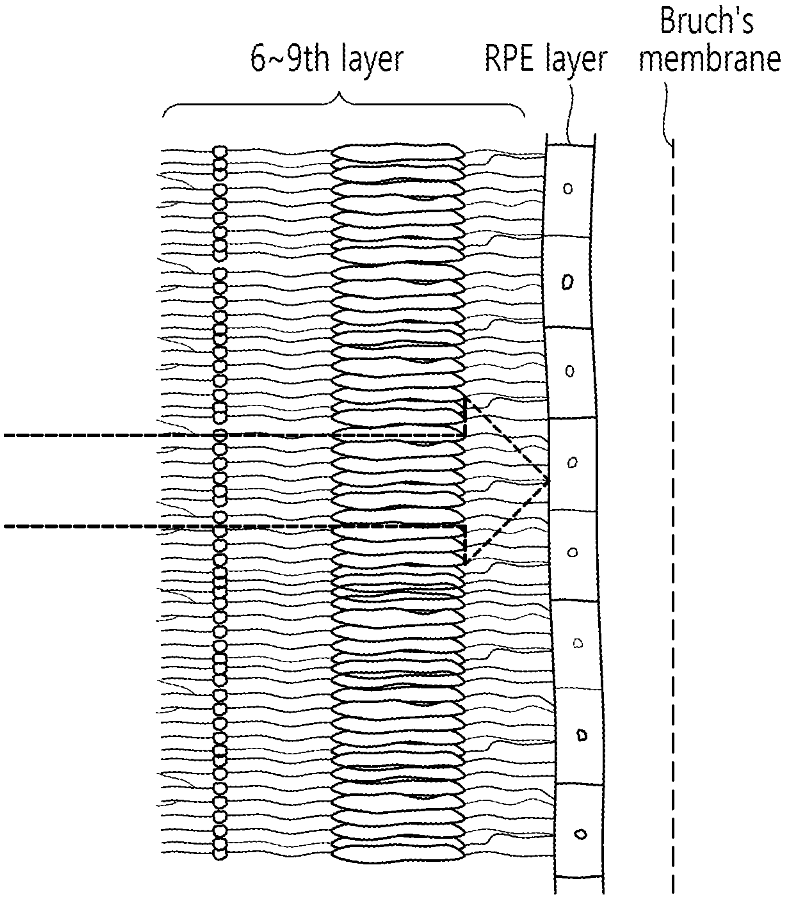
FIG. 3 is an enlarged sectional view of area A of FIG. 2.

FIG. 3 is an enlarged sectional view of area A of FIG. 2. Area A of FIG. 3 is a view illustrating the patient's eyeground tissue corresponding to the treatment area, especially the retina tissue. Such a retina tissue is generally composed of ten layers (in a direction from a retinal surface to a medial side) including an internal limiting layer, a nerve fiber layer, a ganglion cell layer, an inner plexiform layer, an inner nuclear layer, an outer plexiform layer, an outer nuclear layer, an external limiting layer, a photo receptor layer, and a RPE (retinal pigment epithelial) layer.

Among them, the RPE cell layer forms a posterior limiting layer out of ten layers, and is formed in a tight junction structure. The Bruch's membrane is located under the RPE layer. Such a RPE layer is supplied with nutrients and oxygen from a blood vessel located in the choroid, supplies the nutrients to a photo receptor, and functions to discharge waste generated from the photo receptor through the Bruch's membrane.

Unless some of the PRE cells forming the RPE layer perform a normal function, photo receptors located in front of the corresponding RPE cell may not normally be supplied with nutrients and oxygen, thus causing necrosis. In order to treat the necrosis, the ophthalmic treatment apparatus according to this embodiment performs the treatment of inducing the regeneration of a new RPE cell, by selectively radiating the treatment beam to the RPE cell layer to transmit energy.

To be more specific, the treatment beam has a wavelength in a visible ray or near-infrared region. The treatment beam is rarely absorbed by a cell layer (the first cell layer to the ninth cell layer) located in front of the retina and is penetrated. Thereafter, the treatment beam is absorbed by melanosome that is present in the RPE cell. As the amount of energy absorbed by the melanosome increases, the state of the RPE cell is changed due to a rise in temperature, so that the RPE cell having the changed state is replaced by a healthy RPE cell. As the temperature rises, microbubbles are generated on a surface of the melanosome and grow gradually, thus leading to the optional necrosis of an associated RPE cell and inducing a new RPE cell.

However, if an excessively large amount of energy is transmitted to the RPE cell by the treatment beam, a RPE cell corresponding to the target tissue as well as the adjacent photo receptor may be damaged, thus causing impaired vision. In contrast, when energy transmitted to the RPE cell by the treatment beam is not sufficient, no treatment may be performed while the state of the RPE cell is not changed. In other words, it is important to appropriately select the output of the treatment beam radiated to the treatment location so that an appropriate change in state may occur in the target tissue. Therefore, the ophthalmic treatment apparatus according to the present disclosure is provided with the sensing unit 150 that may sense the degree of a change in state of the target tissue by the treatment beam, and may include a guide unit 230 providing information that may guide the treatment operation of the user on the basis of the result sensed by the sensing unit 150.

Turning back to FIG. 2, as described above, the sensing unit 150 is configured to sense a change in state of the target tissue to which energy is transmitted by the treatment beam. The sensing unit 150 of this embodiment is composed of an optoacoustic sensor that measures an optoacoustic level. Such an optoacoustic sensor is provided on the eyepiece part 170 coming into contact with the patient's eye to measure an optoacoustic signal generated during treatment and thereby sense a change in state of the tissue.

To be more specific, if energy below a certain level is transmitted to the RPE cell, a change in state of the RPE cell that may be sensed from an outside does not occur and thereby a new signal is not generated. In contrast, if energy above a certain level is transmitted, microbubbles are generated in the RPE cell and thereby a signal is generated. As the amount of transmitted energy increases, the amount of the microbubbles increases or the bubble is burst, so that the intensity of the signal increases. Moreover, in the case of transmitting an excessively large amount of energy, the RPE cell in the treatment location as well as the adjacent cell is changed in state, so that the intensity of the generated signal may be further increased. Therefore, the sensing unit 150 may measure the signal generated when the treatment beam is radiated, so that it is possible to sense a change in state of the tissue.

Although this embodiment has been described as configuring the sensing unit using the optoacoustic, sensor, the sensing unit may be configured using various devices including a temperature sensor, a photodetector, an interferometer sensor, an optical coherence tomography (OCT) device, an ultrasonic sensor, etc.

Meanwhile, the guide unit 230 provides guide information to which the user may refer while performing the treatment operation, on the basis of the signal sensed by the sensing unit 150. For instance, the guide unit 230 may display information about damage to the tissue by the treatment beam or the treatment intensity to the user (here, the treatment intensity does not mean the absolute value of the treatment beam intensity, and it is determined whether the treatment contents cause a change in state of the tissue corresponding to the treatment target). Alternatively, the guide unit 230 may determine whether the output of the treatment beam is excessive or insufficient on the basis of the information about damage to the tissue, and then may display the determined result to the user. Therefore, the user may check the treatment intensity of the tissue through the guide information provided by the guide unit 230, or may adjust the treatment contents by referring to the checked treatment intensity.

As illustrated in FIG. 2, the guide unit 230 of this embodiment is configured to display information through the display device of the interface unit 20 to the user. Alternatively, in order for the user to check the information through the eyepiece part 170, this may be displayed through the separate display provided in the slit lamp. In addition, it is possible to provide guide information to the user not in a visual method but in an audio or haptic method.

The guide unit 230 may display information about the damage to the tissue using at least one reference value. Here, the reference value may be a value that is set by the signal sensed in the sensing unit when a targeted state change occurs in the tissue by radiating the treatment beam, and may be a reference for determining the degree of the damage to the tissue or the treatment intensity. Furthermore, the guide unit 330 may provide information about the damage to the tissue to the user by comparing the signal value sensed during the treatment with a set reference value.

For instance, it is assumed that the reference value is a value sensed when the tissue is excessively damaged. In this case, if the signal value sensed by the sensing unit during the treatment is guided to be 90 to 100% of the reference value, the user may determine that the output of the radiated treatment beam is excessive during the treatment and thereby the tissue may be excessively damaged. As another example, it is assumed that the reference value is a value sensed when energy is started to be efficiently transmitted to the tissue. In this case, if the signal value sensed in the sensing unit during the treatment is guided to be 50% or less of the reference value, the user may determine that the output of the radiated treatment beam is weak during the treatment and thereby energy transmitted to the tissue is insufficient.

The ophthalmic treatment apparatus according to this embodiment further includes a setting unit 240 for setting the reference value. As illustrated in FIG. 2, the setting unit 240 may be provided in the interface unit 20. The user inputs the reference value or the information corresponding to the reference value through the setting unit 240, and thereby the reference value is set. Although FIG. 2 illustrates that the setting unit and the input unit are separate components, the function of each component will be separately shown, and the setting unit and the input unit may be implemented as one component.

Here, the user may set the reference value in various manners. For instance, the user may set the reference value by directly inputting the reference value itself through the setting unit, on the basis of the user's experience. Alternatively, optimal reference values according to a patient's race, sex, and age are stored in a database of the treatment apparatus. If the user inputs the detailed conditions of the patient through the setting unit, an optimal reference value meeting the corresponding condition may be set.

Even if patients have the same conditions, the intensity of the signal generated when the targeted state change of the tissue occurs may vary depending on the patient's condition, the shape and size of the eyeball. Therefore, the ophthalmic treatment apparatus according to this embodiment is configured to individually set the reference value according to each patient before the treatment is performed.

Figure 4:
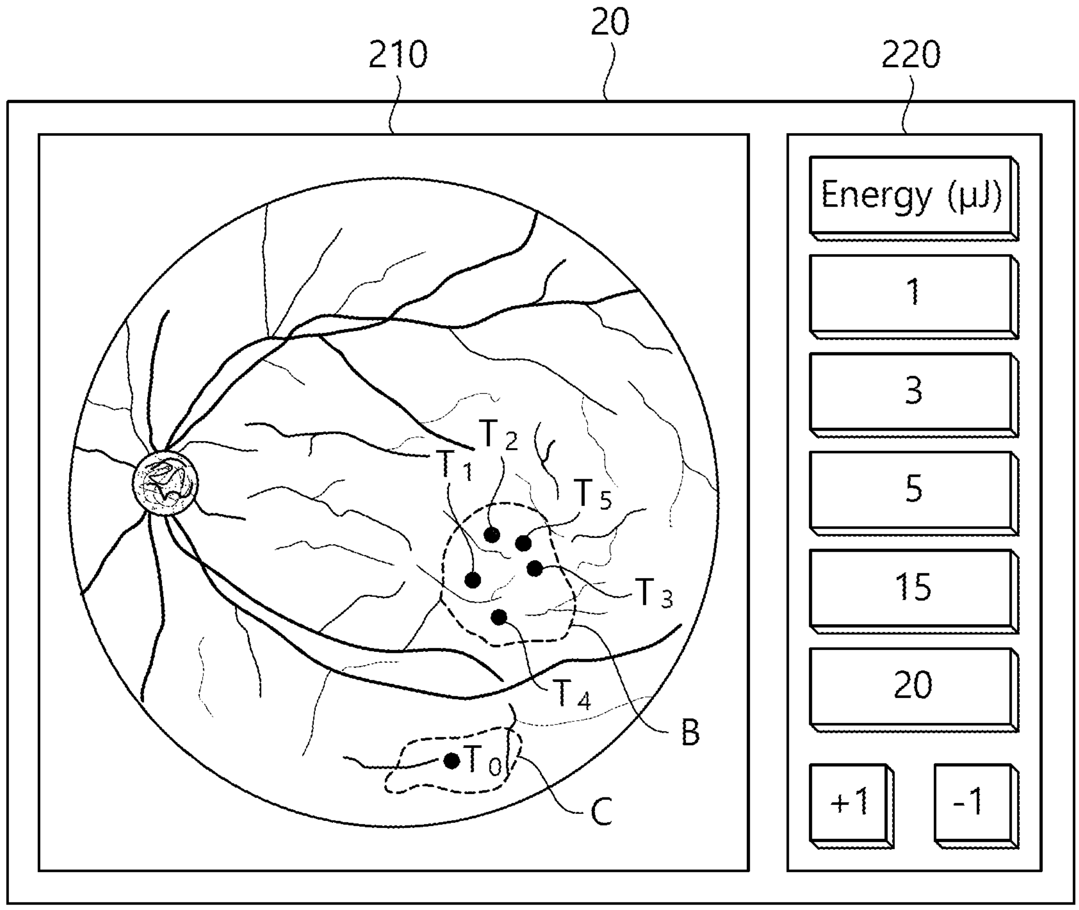
FIG. 4 is a diagram illustrating an interface unit in which an eyeground image and a treatment beam parameter menu are displayed.
Figure 5:
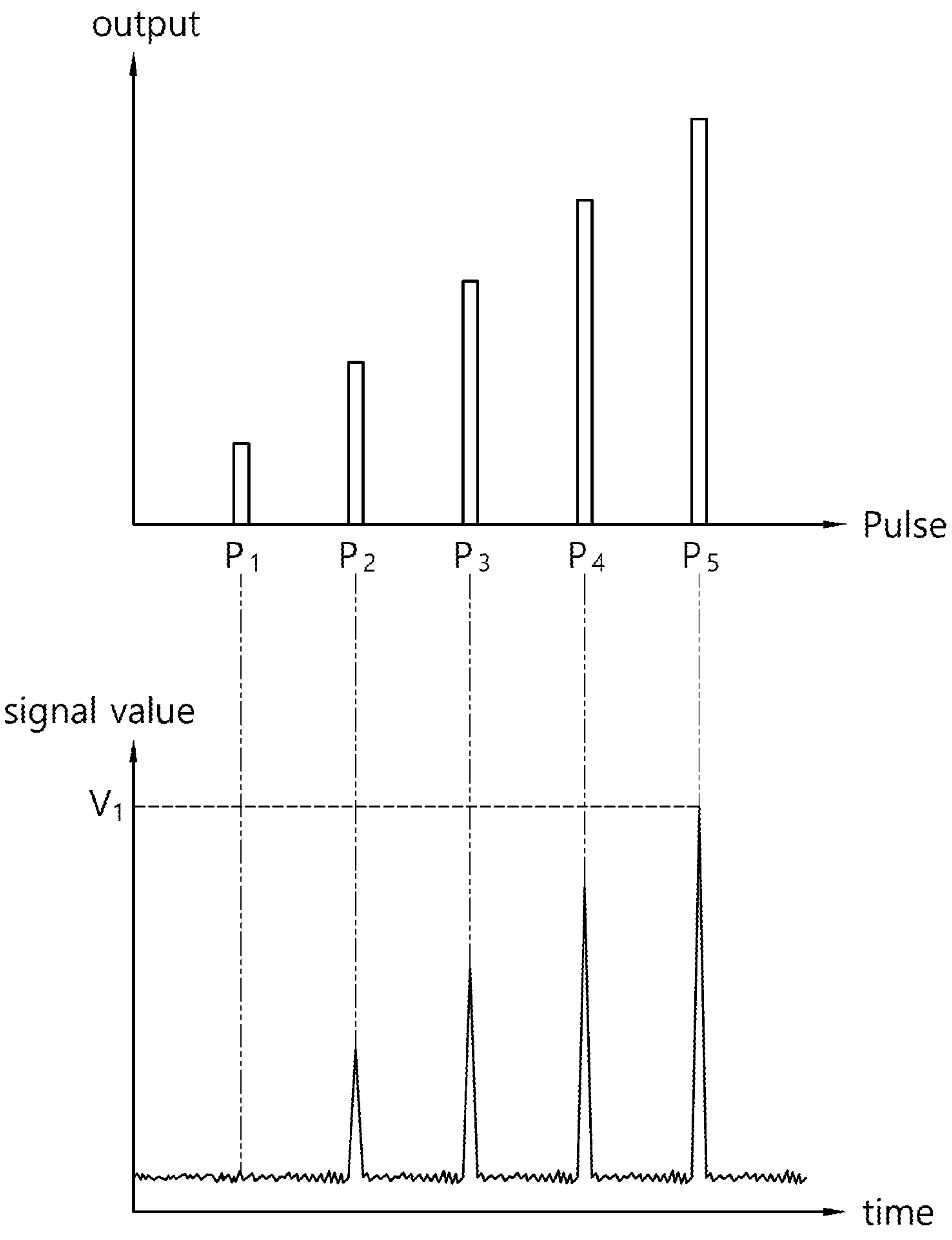
FIG. 5 is a graph showing a pattern of a treatment beam radiated to a test area and a signal value.

FIG. 4 is a diagram illustrating the interface unit in which an eyeground image and a treatment beam parameter menu are displayed, and FIG. 5 is a graph showing a pattern of a treatment beam radiated to a test area and a sensed signal value. Hereinafter, an example of setting the above-described reference value will be described in detail with reference to FIGS. 4 and 5.

The interface unit 20 illustrated in FIG. 4 has the display unit 210 on which the image of the patient's eyeground photographed by the imaging unit is displayed, and the input unit 220 which may select the output of the treatment beam. This embodiment may set the signal value, which is generated when over treatment is performed and the tissue is excessively damaged, as the reference value. Therefore, the user adjusts the input unit 220 to transmit excessive energy to the tissue and thereby over-treat the tissue, and a process of measuring the signal value through the sensing unit 150 is performed. Since it is undesirable to perform such a process in the treatment area B in which the lesion is located, the above process may be performed in a separate test area located outside the treatment area.

To be more specific, the user radiates the treatment beam multiple times to any location T0 in the test area C. This embodiment is configured to radiate the treatment beam multiple times to the same location T0 in the test area C, but may radiate the treatment beam while changing the radiating location in the test area C. In this case, the user may manipulate the input unit 220 to arbitrarily adjust the output of the treatment beam and then radiate the treatment beam. As illustrated in FIG. 5, it is preferable to radiate the treatment beam in a pattern where the output of the treatment beam is gradually increased. In this case, it is possible to sense a time when over treatment is started, that is, a time when a targeted state change occurs.

The time when the targeted state change occurs may be determined depending on whether white burn occurs on the eyeground of the patient. The treatment apparatus of this embodiment treats the RPE cell layer located inside the eyeground as the target tissue. Thus, if the white burn occurs even on the surface of the retina, it may be determined that the over treatment is performed. Therefore, the user determines that the targeted state change occurs, if the white burn is observed on the eyeground image of the interface unit or through the slit lamp, while the treatment beam is radiated to the test area.

As illustrated in FIG. 5, while the treatment beam is radiated to the test area multiple times, the sensing unit 150 senses a signal generated due to the change in state of the tissue. In FIG. 5, when the fifth treatment beam P5 is radiated, the white burn was observed in the patient's eyeground. Therefore, the user selects the fifth treatment beam through the setting unit, or inputs the output of the fifth treatment beam, so that the reference value may be a signal value V1 generated when the associated treatment beam is radiated.

As such, if the reference value is determined, the guide unit 230 may display information about the damage to the tissue by the treatment beam during the treatment using the reference value in various manners. Hereinafter, various examples of the guide unit will be described in detail with reference to FIGS. 6 to 9.

Figure 6:
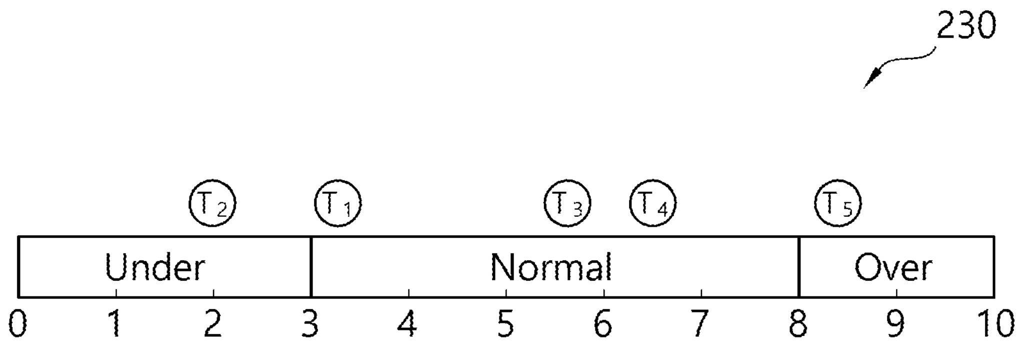
FIG. 6 is a diagram illustrating an example of a guide unit of FIG. 2.

First, FIG. 6 is a diagram illustrating an example of a guide unit of FIG. 2. The guide unit 230 may have grade sections divided to indicate the degree of the damage to the tissue using the set reference value. As an example, as illustrated in FIG. 6, it is possible to have ten grades according to a ratio to the set reference value V1. Here, the respective grade sections may be divided into the same ratio sections, and be divided in consideration of a weight. Here, it may be determined that first to third grades are under treatment grades, fourth to eighth, grades are normal treatment grades, and ninth and tenth grades are over treatment grades (this may vary depending on the reference value and the grade division method).

Furthermore, if the treatment beam is radiated, the guide unit 230 cumulatively displays signal values generated in the tissue by respective treatment beams on graphic indicating the above-described grade sections. In FIG. 6, when the treatment beam is sequentially radiated to five treatment locations T1 to T5 during the treatment, the signal value generated in each location is indicated. In this case, it can be seen that the treatment is performed in the normal range in the first treatment location T1, but the treatment is not properly performed in the second treatment location T2. Therefore, the user may adjust to increase the output of the treatment beam, with reference to the contents displayed in the guide unit. Subsequently, it can be seen that the normal treatment is performed in the third and fourth treatment locations T3 and T4, and the over treatment is performed in the fifth treatment location T5.

Figure 7:
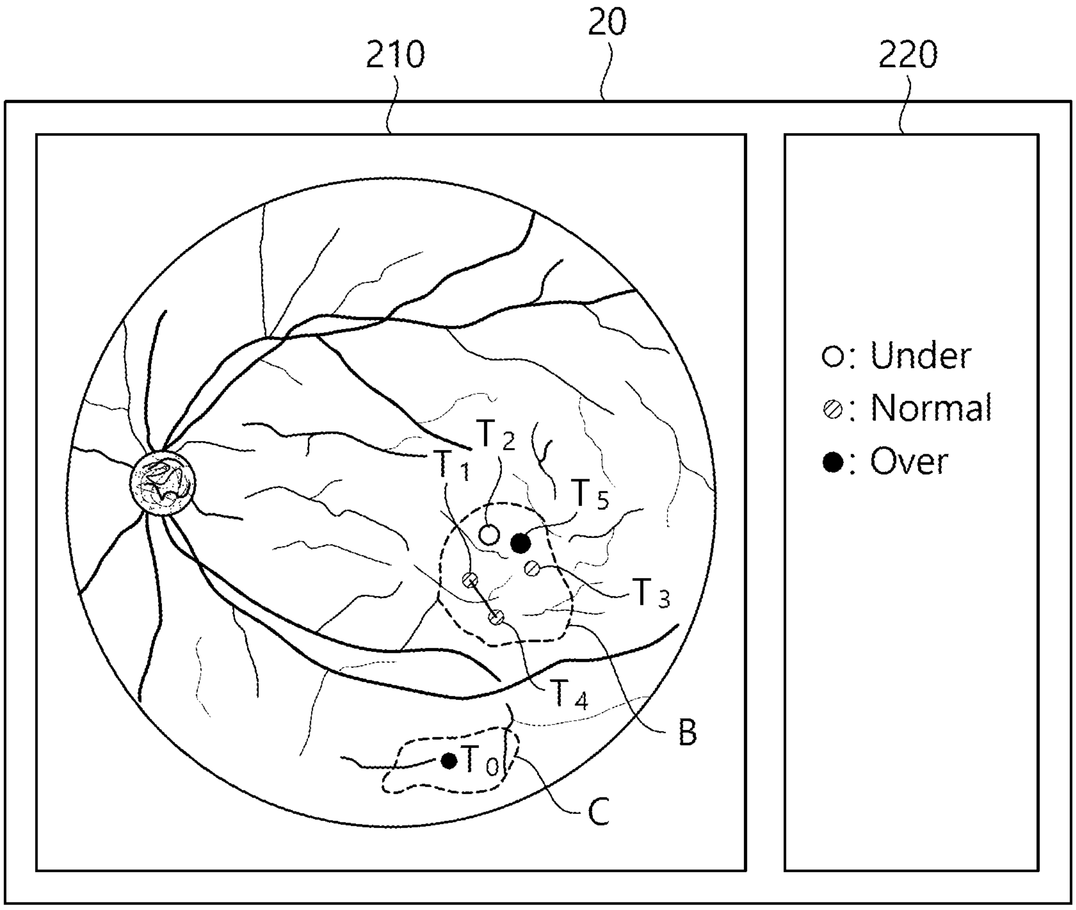
FIG. 7 is a diagram illustrating another example of a guide unit of FIG. 2.

FIG. 7 is a diagram illustrating another example of the guide unit of FIG. 2. The guide unit of FIG. 6 displays the damage information by each treatment beam on the grade section graphic, whereas the guide unit of FIG. 7 displays the damage information in a location where the treatment beam is radiated on the eyeground image. As illustrated in FIG. 7, the spot of the treatment location may be differently displayed according to the under treatment state, the normal treatment state, and the over treatment state. For example, the spot of the treatment location may be differently displayed using colors, shades, or shapes. Furthermore, the signal value generated by each treatment beam is compared with the grade section to determine the damage information, and the spot corresponding to the associated damage information is displayed on the eyeground image, thus guiding the user.

Figure 8:
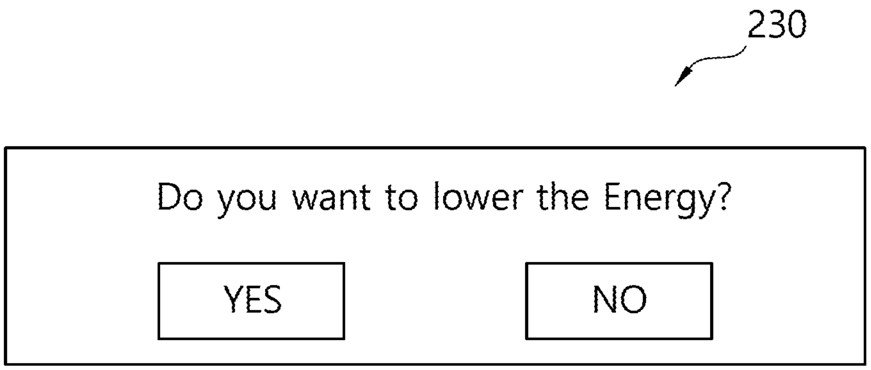
FIG. 8 is a diagram illustrating a further example of a guide unit of FIG. 2.

FIG. 8 is a diagram illustrating a further example of the guide unit of FIG. 2. In FIG. 8 as well as FIG. 6, the guide unit 230 itself may determine the information of the damage to the tissue (or the treatment intensity) on the basis of the reference value and the measured signal value, and may perform the display suggesting the adjustment of the parameter, such as the output of the treatment beam, to the user. For example, if it is determined that the over treatment is performed in the fifth treatment location T5 as illustrated in FIG. 6, the guide unit 230 may suggest that the user lowers the energy of the treatment beam as illustrated in FIG. 8, thus guiding the user's treatment operation.

The display examples of the guide unit illustrated in FIGS. 6 to 8 may be alternatively performed, but the display may be simultaneously performed using separate windows.

Figure 9:
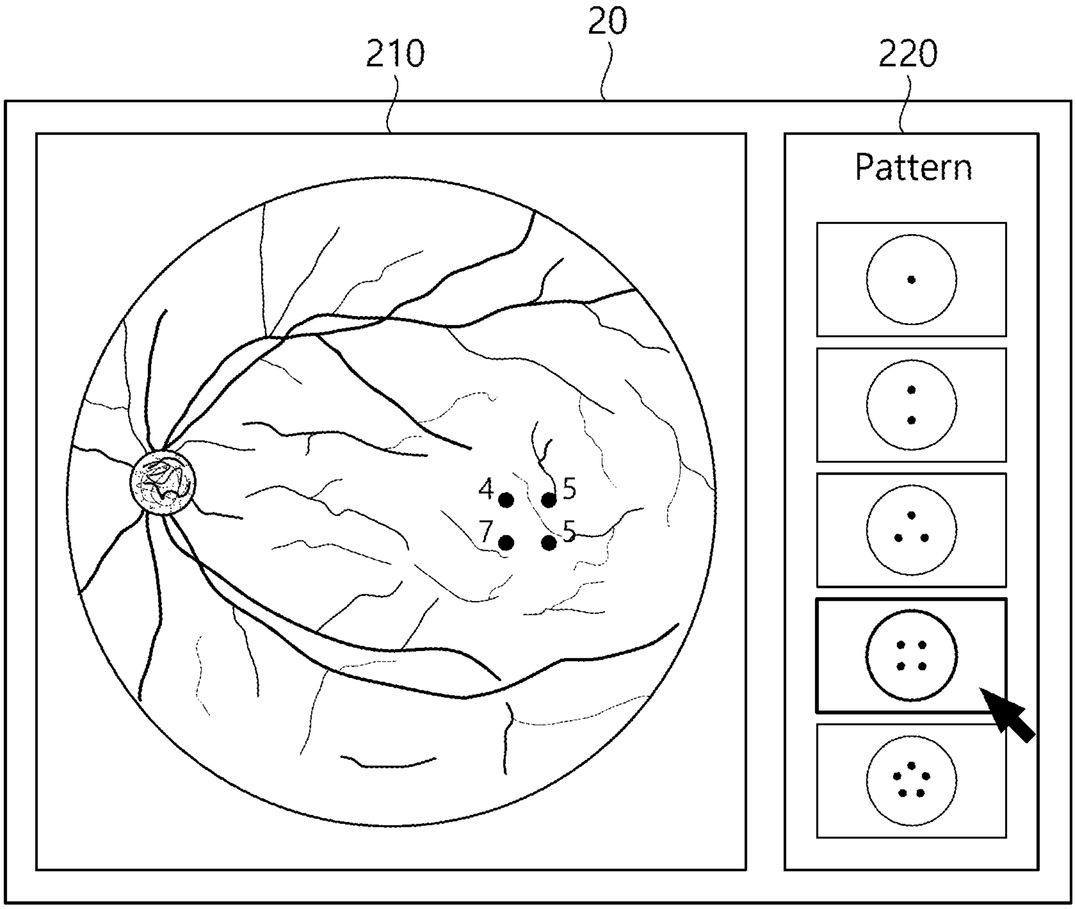
FIG. 9 is a diagram illustrating an interface unit in which an eyeground image and a treatment beam pattern menu are displayed.

Meanwhile, FIG. 9 is a diagram illustrating the interface unit in which the eyeground image and the treatment beam pattern menu are displayed. When the treatment beam is radiated in the form of a pattern, the treatment beam may be sequentially radiated to a plurality of treatment locations forming the pattern in response to one radiation command. In this case, as illustrated in FIG. 9, treatment beam radiating locations according to the pattern selected on the eyeground image may be displayed, and the information about the tissue damage in each location may be displayed on the eyeground image on the basis of the signal value generated by each treatment beam. Although in FIG. 9, the damage information in a location where the treatment beam is radiated is displayed with each grade section, the user's treatment may be guided by displaying a corresponding location with a different color depending on the under treatment, the normal treatment, or the over treatment.

Hereinbefore, various display methods of the guide unit have been mainly described. In the above description, an example where the guide unit displays the degree of the damage to the tissue using one reference value has been mainly described. However, it is possible to display the degree of the damage to the tissue using a plurality of reference values. For example, a first reference value and a second reference value may be set through the setting unit, and the guide unit may guide the treatment operation of the user using the first reference value and the second reference value.

Here, as described above, the first reference value is a value for determining whether energy is excessively transmitted to the tissue and thereby the over treatment is performed. Furthermore, the second reference value is a value for determining whether energy is efficiently transmitted to the tissue. If the amount of energy transmitted to the tissue by the treatment beam is small, temperature may temporarily rise before thermal radiation, but the state of the tissue may not be changed. Therefore, the efficient transmission of energy to the tissue means that energy sufficient to cause a change in state of the tissue is transmitted to the tissue. Therefore, the guide unit may compare the signal value sensed during treatment with the first reference value to determine whether the over treatment is performed, and may compare the signal value with the second reference value to determine whether the treatment intensity is insufficient.

The second reference value may be a signal sensed when energy is transmitted by the treatment beam and thereby a change in state of the tissue is started. In other words, a change in state for setting the second reference value is very delicately made, unlike the first reference value. Therefore, in this embodiment, in order to easily observe a delicate state change of the tissue located inside the eyeground, angiography is used. Thereby, it is possible to determine whether energy is efficiently transmitted to the tissue.

To be more specific, the step of setting the second reference value is performed by radiating a plurality of treatment beams to a test area C separated from a treatment area B, as in FIG. 5. In this case, the change in state of the location where the treatment beam is radiated is observed using the angiography. As the treatment beam is radiated while the output of the treatment beam is gradually increased, the change in state of the tissue (e.g. blood penetration, new blood flow formation, etc.) is sensed through the angiography. In this case, it is determined that the targeted state change is made, and the signal value sensed by the sensing unit may be set as the second reference value when the corresponding treatment beam is radiated.

As such, in the case of setting the first reference value and the second reference value through the setting unit 240, the guide unit 230 may provide guide information during treatment using the first reference value and the second reference value. For example, when the grade sections indicating the degree of damage to the tissue are divided as illustrated in FIG. 6, the first reference value may be used as an upper boundary value (corresponding to 10 of FIG. 6) in a highest damage section, and the second reference value may be used as a boundary value (corresponding to 3 of FIG. 6) dividing the normal treatment grade from the under treatment grade. In addition, a plurality of reference values may be used in various ways depending on a form in which the guide unit displays the degree of damage to the tissue.

Hereinafter, the control method of the ophthalmic treatment apparatus and the treatment method using the same according to this embodiment will be described in detail, with reference to FIGS. 10 and 11.

Figure 10:
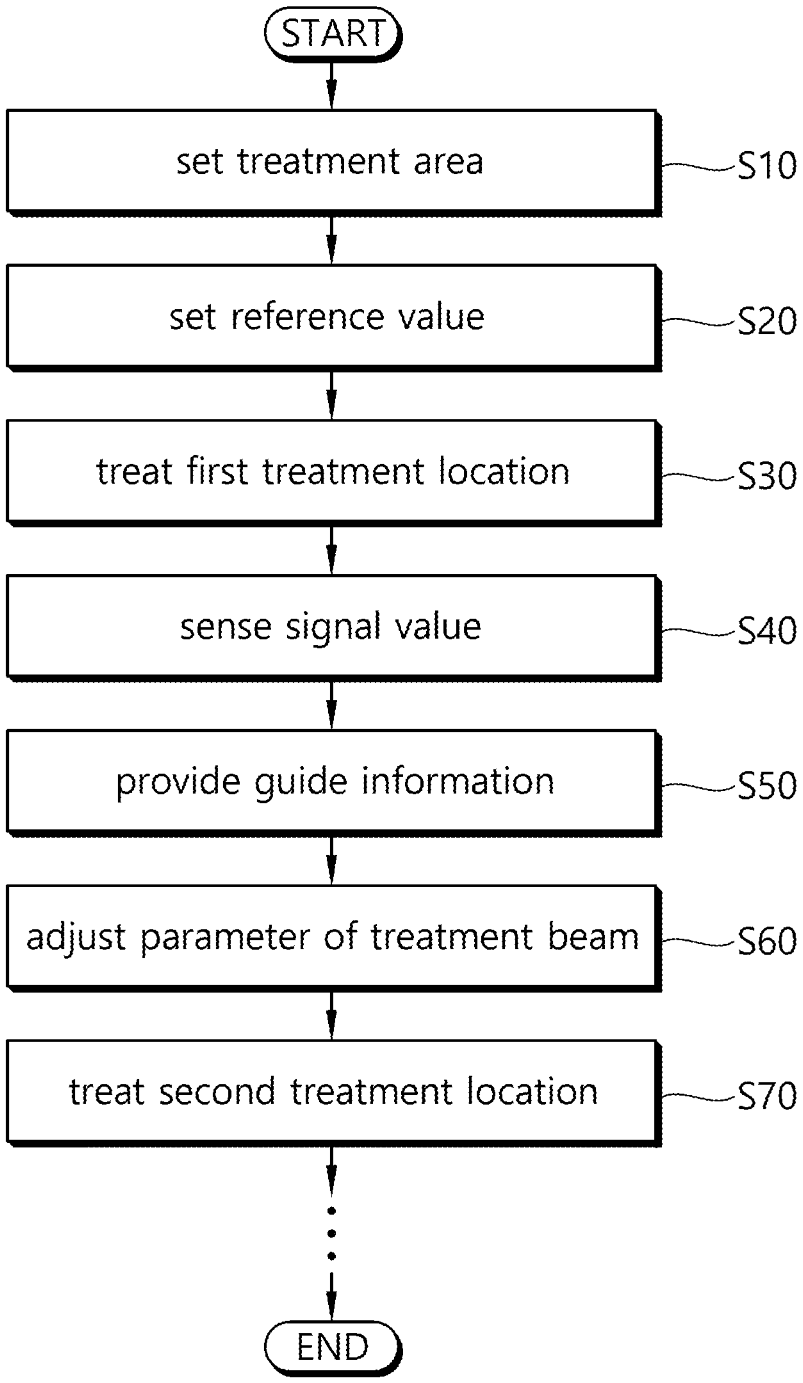
FIG. 10 is a flowchart illustrating a method of controlling an ophthalmic treatment apparatus in accordance with an embodiment.

FIG. 10 is a flowchart illustrating a method of controlling an ophthalmic treatment apparatus in accordance with an embodiment. As illustrated in FIG. 10, the user diagnoses the patient's lesion and then determines the treatment area of the eyeground (S10). While the treatment area is determined, various treatment contents including the treatment mode, the radiating pattern of the treatment beam, the radiating location of the treatment beam are determined, and required contents may be input through the input unit.

Furthermore, if the treatment area is determined, the step of setting the reference value through the setting unit is performed (S20). The reference value is a value for guiding the degree of damage to the tissue as described above, and may be set in various ways. The user may input the reference value on the basis of an empirical rule, may set an appropriate reference value stored in the database on the basis of the patient's properties input by the user, and may set the reference value using the reference value that is set in the previous treatment in the stored patient's treatment history. In this embodiment, the reference value may be set by radiating the treatment beam to an associated patient under the same condition that treatment is performed.

Figure 11:
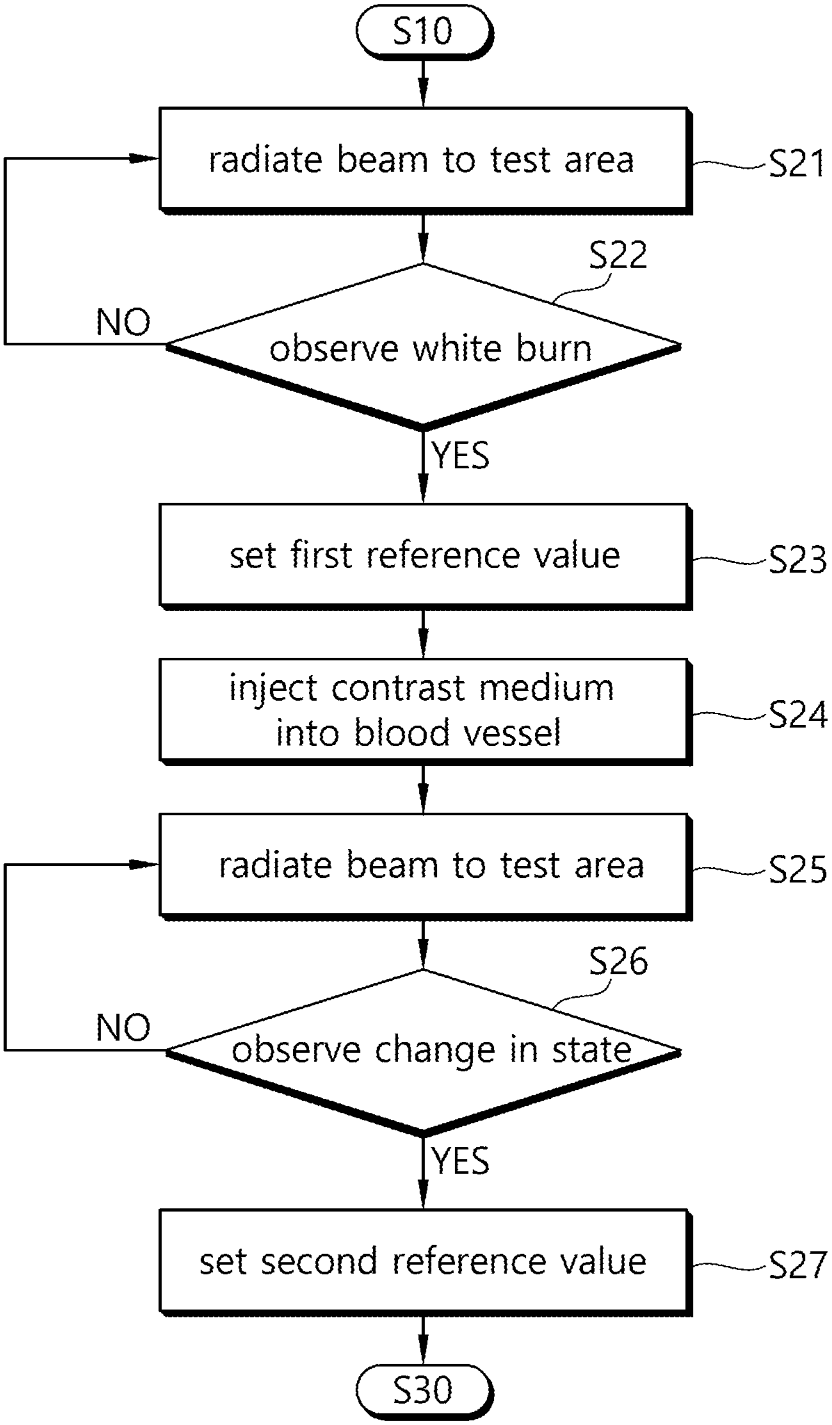
FIG. 11 is a flowchart illustrating a reference value setting step of FIG. 10 in more detail.

FIG. 11 is a flowchart illustrating the reference value setting step of FIG. 10 in more detail. The reference value setting step of FIG. 11 is configured to sequentially set the first reference value and the second reference value.

First, in order to set the first reference value, the treatment beam is radiated to the test area multiple times (S21). Here, the test area C is an area that is separated from the treatment area B in which the lesion is located in S10. While the treatment beam is radiated to the test area C, the user observes whether the white burn occurs in the eyeground through the slit lamp 10 or the eyeground image displayed in the display unit 210 (S22). When the white burn is not observed, the user repeats the step of S21 while increasing the output of the treatment beam. Furthermore, when the white burn is observed, the first reference value is set using the signal value that is sensed when the white burn occurs (S23).

Subsequently, a contrast medium is injected into a blood vessel to set the second reference value using the angiography (S24). As in S21, the treatment beam is radiated to the test area multiple times (S25). The user observes whether the change in state of the tissue inside the eyeground (e.g. blood penetration, new blood flow formation, etc.) occurs through the angiography while the treatment bean is radiated (S26). When such a change in state does not occur, the step of S25 is repeated while the output of the treatment beam is increased. Furthermore, when the change in state is observed by the angiography, the second reference value is set using the signal value sensed when the state is changed (S27).

If the reference values are set through the above-described reference value setting step S20, the treatment beam is radiated to each treatment location in the treatment area, thus performing treatment. First, the treatment is performed by radiating the treatment beam to the first treatment location (S30). In this case, the output of the treatment beam may be radiated on the basis of the parameter that is input by the user through the input unit 220.

If the treatment beam is radiated to the first treatment location, the sensing unit 150 measures a signal generated by the change in state of the tissue in an associated location (S40). Furthermore, the guide unit 230 displays the guide information to the user using the signal value sensed by the sensing unit and the set reference values (S50).

In the step of displaying the guide information, the degree of damage to the tissue may be set in a plurality of grade sections using the first reference value and the second reference value and the degree of damage in the first treatment location may be indicated on the corresponding grade (see FIG. 6), the damage information may be displayed using the color or shape of the spot indicating the location where the treatment beam is radiated on the eyeground image (see FIG. 7), and it may be configured to suggest that the user adjusts the parameter of the treatment beam according to the calculation of the guide unit (see FIG. 8). In addition, the guide information may be displayed in various manners.

As described above, if the guide information about the treatment in the first treatment location is provided, the user may perform the step of determining the guide information and adjusting the parameter of the treatment beam (S60). This step is not, an essential step, and may be selectively performed according to the user's determination on the basis of the guide information. The treatment is performed after the treatment location is changed from the first treatment location to the second treatment location (S70), and the above-described steps S40 to S60 may be repeated. In this case, treatment may be performed using the treatment beam of the adjusted parameter in the second treatment location, so that it is possible to perform a proper treatment on the basis of the treatment result of the preceding treatment location.

The control method of the ophthalmic treatment apparatus and the treatment method using the same guide information about damage to the tissue due to the radiation of each treatment beam, so that the user can perform the treatment on the basis of the damage information, thus minimizing a difference in treatment result according to a user's skill, and allowing proper treatment to be performed even if properties are different according to the location of the tissue.

Although the treatment apparatus for treating the eyeground lesion has been mainly described in the foregoing embodiment, the present disclosure may be applied to a treatment apparatus for treating lesions other than the eyeground, for example a glaucoma treatment apparatus or a skin treatment apparatus. In this case, the apparatus described in the foregoing embodiment is basically applied, but the configuration of the sensing unit for sensing the information about the change in state of the tissue and the method of setting the reference value for determining the damage information may be changed depending on the lesion and then may be easily implemented.

For example, when the present disclosure is applied to the glaucoma treatment apparatus, the sensing unit may be configured using the photodetector, the interferometer sensor, the optoacoustic sensor, etc. Furthermore, the reference value may be set as the first reference value when discoloration is observed in the TM tissue during the radiation of a test beam. Alternatively, it is possible to configure such that the first reference value is set using a signal value in a state where the macro bubble is sensed through the sensing unit when the test beam is radiated, and the second reference value is set using a signal value in a state where the micro bubble is sensed.

As another example, when the present disclosure is applied to the skin treatment apparatus, the sensing unit may use the ultrasonic sensor or the photodetector. Furthermore, each of the first and second reference values may be set on the basis of the increase or decrease, gradient, or inflection point of a signal detected by the sensing unit.

Although the present disclosure was described in detail with reference to specific embodiments, the present disclosure is not limited to these embodiments. It is apparent to those skilled in the art that the present disclosure may be changed and modified in various ways without departing from the scope of the present disclosure, which is described in the following claims.

The invention claimed is:

1. An ophthalmic treatment apparatus comprising:

a treatment beam generation unit for generating a treatment beam which is radiated to a treatment area;

a sensing unit for sensing a signal generated as a state of an eye tissue of the treatment area changes due to each treatment beam radiated to the treatment area;

a guide unit for displaying, to a user, information about damage to the eye tissue caused by each treatment beam radiated on the basis of the signal sensed by the sensing unit; and a setting unit for setting at least one reference value using a signal sensed by the sensing unit while each treatment beam is radiated to a test area, wherein the guide unit determines a grade indicating a degree of damage to the eye tissue caused by each treatment beam using the at least one reference value, and displays the determined grade at a corresponding spot in the treatment area of an eyeground image, each spot corresponding to a respective treatment beam, wherein the grade indicating the degree of damage to the eye tissue is determined by comparing the signal sensed by the sensing unit during treatment with the at least one reference value.

2. The ophthalmic treatment apparatus of claim 1, wherein the at least one reference value is set using the signal sensed by the sensing unit when a targeted state change occurs in a tissue of the test area by the treatment beam.

3. The ophthalmic treatment apparatus of claim 2, wherein the treatment beam radiated to the test area is in a form of a plurality of pulses whose outputs are sequentially increased.

4. The ophthalmic treatment apparatus of claim 1, wherein the at least one reference value is a signal value which senses a signal generated from the eye tissue when the eye tissue undergoes over treatment, and the guide unit compares the signal sensed by the sensing unit during the treatment with the reference value to display the information about damage to the eye tissue in the treatment area to the user.

5. The ophthalmic treatment apparatus of claim 4, wherein the guide unit suggests that the user lowers an intensity of the treatment beam, when it is determined that the eye tissue undergoes the over treatment on the basis of the signal sensed by the sensing unit during the treatment.

6. The ophthalmic treatment apparatus of claim 1, wherein the at least one reference value comprises a first reference value corresponding to a signal generated in the eye tissue when the eye tissue undergoes over treatment, and a second reference value corresponding to a signal generated in the eye tissue when energy is efficiently delivered to the eye tissue, and the guide unit compares the signal value of the signal sensed by the sensing unit during the treatment with each of the first reference value and the second reference value to determine the grade indicating the degree of damage to the eye tissue and display the grade as the information about damage to the eye tissue to the user.

7. The ophthalmic treatment apparatus of claim 6, wherein the guide unit determines a grade section indicating a degree of damage to the eye tissue using the first reference value and the second reference value, and the degree of damage to the eye tissue caused by an associated treatment beam on the basis of the signal sensed by the sensing unit during the treatment is indicated by a grade of the grade section.

8. The ophthalmic treatment apparatus of claim 7, wherein a highest damage grade in the grade section comprises the first reference value, and a lowest damage grade does not comprise the second reference value.

9. The ophthalmic treatment apparatus of claim 1, wherein, when the treatment beam is radiated to a plurality of locations in the treatment area, the guide unit displays information about damage to the eye tissue in an associated location for the respective locations where the treatment beam is radiated.

10. The ophthalmic treatment apparatus of claim 1, wherein the at least one reference value comprises a first reference value corresponding to a signal generated in the eye tissue when a targeted state change occurs in the eye tissue, the targeted state change including an occurrence of white burn on an eyeground, and a second reference value corresponding to a signal generated in the eye tissue when a change in state of the eye tissue occurs, the change in state of the eye tissue including blood penetration and new blood flow formation.

11. The ophthalmic treatment apparatus of claim 6, wherein the guide unit determines a plurality of grade sections each indicating a degree of damage to the eye tissue using the first reference value and the second reference value.

* * * * *